United States Patent [19]

Seppelt et al.

[11] Patent Number: 4,855,140

[45] Date of Patent: Aug. 8, 1989

[54] O-(O-ETHYL-S-ALKYLPHOSPHORYL)-O-(CARBAMYL)-PYROCATECHOL DERIVATIVES

[75] Inventors: Wolfgang Seppelt, Bobenheim-Roxheim; Linhard Sproesser, Bad Doerkheim; Siegfried Kersten, Frankenthal; Peter Hofmeister, Neustadt; Christoph Kuenast, Otterstadt, all of Fed. Rep. of Germany

[73] Assignee: Basf Aktiengesellschaft, Rheinland-Pfalz, Fed. Rep. of Germany

[21] Appl. No.: 249,320

[22] Filed: Sep. 26, 1988

[30] Foreign Application Priority Data

Sep. 26, 1987 [DE] Fed. Rep. of Germany ....... 3732527

[51] Int. Cl.$^4$ ............................................. A01N 25/00
[52] U.S. Cl. .................................... 424/405; 514/109; 514/119; 514/478; 514/490
[58] Field of Search ............... 424/405, 417, 418, 421; 514/109, 119, 478, 490

[56] References Cited

PUBLICATIONS

J. Agr. Food Chem., vol. 20, No. 3, 1972, Hetnarski, et al., Preparation of Properties of Phenyl . . . , pp. 543–546.

Primary Examiner—Thurman K. Page
Assistant Examiner—P. L. Prater
Attorney, Agent, or Firm—Oblon, Spivak, McClelland, Maier & Neustadt

[57] ABSTRACT

O-(O-ethyl-S-alkylphosphoryl)-O-(carbamoyl)-pyrocatechol derivatives of the formula I

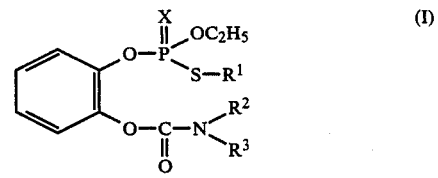

where $R^1$ is $C_1$–$C_4$-alkyl, $R^2$ is hydrogen, $C_1$–$C_4$-alkyl, and X is oxygen or sulfur, and methods of combating pests with effective amounts of I.

5 Claims, No Drawings

O-(O-ETHYL-S-ALKYLPHOSPHORYL)-O-(CARBAMYL)-PYROCATECHOL DERIVATIVES

The present invention relates to novel O-(O-ethyl-S-alkylphosphoryl)-O-(carbamyl)-pyrocatechol derivatives of the general formula I

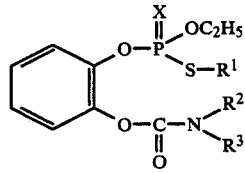

(I)

where $R^1$ is $C_1$-$C_4$-alkyl, $R^2$ is hydrogen, $C_1$-$C_4$-alkyl or $C_1$-$C_4$-alkoxy, $R^3$ is hydrogen or $C_1$-$C_4$-alkyl and X is oxygen or sulfur.

The present invention furthermore relates to the preparation of the compounds I, pesticides which contain the compounds I as active ingredients and a method for controlling pests.

J. Agr. Food Chem. 20 (3) (1972), 543–546 discloses compounds of Type I which do not carry a thioester ($R^1$—S) radical in the phosphate moiety of the molecule, as insecticides, in particular against flies. However, the action of these compounds is unsatisfactory.

It is an object of the present invention to provide novel O-(O-ethyl-S-alkylphosphoryl)-O-(carbamyl)-pyrocatechol derivatives having an improved action.

We have found that this object is achieved by the novel O-(O-ethyl-S-alkylphosphoryl)-O-(carbamyl)-pyrocatechol derivatives I defined at the outset, processes for their preparation, pesticides which contain the compounds I as active ingredients and a method for controlling pests using O-(O-ethyl-S-alkylphosphoryl)-O-(carbamyl)-pyrocatechol derivatives I.

The substituents in formula I have the following specific meanings:

$R^1$ is $C_1$-$C_4$-alkyl, preferably $C_3$- or $C_4$-alkyl, such as n-propyl, isopropyl, n-butyl, isobutyl, sec-butyl or tert-butyl, particularly preferably n-propyl or sec-butyl, $R^2$ is hydrogen, $C_1$-$C_4$-alkyl, preferably $C_1$- or $C_2$-alkyl, particularly preferably methyl, or $C_1$-$C_4$-alkoxy, preferably $C_1$- or $C_2$-alkoxy, such as methoxy or ethoxy, $R^3$ is hydrogen or $C_1$-$C_4$-alkyl, preferably $C_1$- or $C_2$-alkyl, particularly preferably methyl, and X is oxygen or sulfur.

The compounds I are obtainable by the following method:

An O-carbamylpyrocatechol II and an O-ethyl-S-alkylphosphoryl halide III are reacted in the presence of a base at from —20° to 250° C., preferably from 20° to 120° C., in accordance with the following equation:

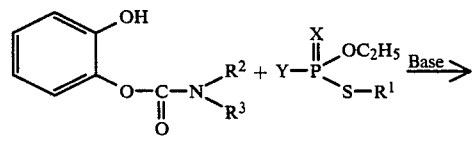

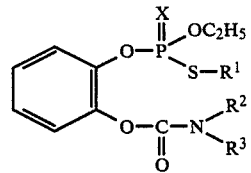

(I)

Y=fluorine, chlorine, bromine or iodine.

The O-carbamylpyrocatechol derivatives II are disclosed in J. Prakt. Chem. 313 (1971), 626 et seq or can be obtained by the methods described there.

Some of the O-ethyl-S-alkylphosphoryl halides III are disclosed in Houben-Weyl, Methoden der organischen Chemie, Vol. 12/2 (1964), 621 et seq, and Vol. E/2 (1982), 676, Thieme-Verlag, or can be obtained by the methods conventionally used there.

For the preparation of the novel compounds I by the method described above, the starting materials are usually used in a stoichiometric ratio. However, an excess of one or other of the components may be quite advantageous in specific cases.

Usually, not less than equivalent amounts of base are added to II and/or III, although the said base may also be used in excess or, if required, also as a solvent. Examples of suitable bases are hydroxides of alkali metals and of alkaline earth metals, such as sodium hydroxide, potassium hydroxide and calcium hydroxide, alcoholates of alkali metals and of alkaline earth metals, such as sodium methylate, sodium ethylate, calcium methanolate or potassium tert-butylate, alkali metal and alkaline earth metal hydrides, such as sodium hydride, potassium hydride or calcium hydride, alkali metal and alkaline earth metal carbonates, such as sodium carbonate, potassium carbonate or calcium carbonate, aliphatic amines, such as dimethylamine, triethylamine or diisopropylamine, heterocyclic amines, such as piperidine, piperazine or pyrrolidine, aromatic amines, such as pyridine or pyrrole, and, if desired, also alkyllithium compounds, such as n-butyllithium.

The reaction is advantageously carried out in a solvent or diluent. Examples of suitable substances for this purpose are aliphatic hydrocarbons, such as n-pentane, n-hexane, the hexane isomer mixture and petroleum ether, aromatic hydrocarbons, such as benzene, toluene, xylenes and their isomer mixtures and gasoline, chlorohydrocarbons, such as methylene chloride, chloroform and carbon tetrachloride, aromatic chlorohydrocarbons, such as chlorobenzene, alcohols, such as methanol, ethanol, n-propanol and isopropanol, ethers, such as diethyl ether, di-n-butyl ether, methyl tert-butyl ether, tetrahydrofuran and dioxane, ketones, such as acetone, methyl ethyl ketone, methyl isopropyl ketone and methyl isobutyl ketone, nitriles, such as acetonitrile and propionitrile, and aprotic dipolar solvents, such as dimethylformamide, dimethylacetamide, dimethyl sulfoxide or pyridine. Mixtures of these substances can also be used as solvents and diluents.

The reactions usually take place at a sufficient velocity at above —20° C. In general, there is no need to exceed 120° C. Since in some cases the reaction takes place with evolution of heat, it may be advantageous to provide a means of cooling.

The reaction mixtures are worked up in a conventional manner, for example by the addition of water, separation of the phases and column chromatography. Some of the novel compounds of the formula I are obtained in the form of colourless or slightly brownish, viscous oils, which can be freed from the final volatile constituents by prolonged heating at moderately elevated temperatures under reduced pressure (incipient distillation) and can be purified in this manner. If the compounds of the formula I are obtained in crystalline form, they can be purified by recrystallization.

The O-(O-ethyl-S-alkylphosphoryl)-O-(carbamoyl)-pyrocatechol derivatives of the general formula I are suitable for effectively combating pests from the class of insects, aracnnida and nematodes. They may be used as pesticides for protecting crops, and in the hygiene, stores protection and veterinary sectors.

Examples of injurious insects from the Lepidoptera order are *Plutella maculipennis, Leucoptera coffeella, Hyponomeuta malinellus, Argyresthia conjugella, Sitotroga cerealella, Phthorimaea operculella, Capua reticulana, Sparganothis pilleriana, Cacoecia murinana, Tortrix viridana, Clysia ambiguella, Evetria buoliana, Polychrosis botrana, Cydia pomonella, Laspeyresia molesta, Laspeyresia funebra, Ostrinia nubilalis, Loxostege sticticalis, Ephestia kuehniella, Chilo suppressalis, Galleria mellonella, Malacosoma neustria, Dendrolimus pini, Thaumatopoea pityocampa, Phalera bucephela, Cheimatobia brumata, Hibernia defoliaria, Bupalus pinarius, Hyphantria cunea, Agrotis segetum, Agrotis ypsilon, Barathra brassicae, Cirphis unipuncta, Prodenia litura, Laphygma exigua, Panolis flammea, Earis insulana, Plusia gamma, Alabama argillacea, Lymantria dispar, Lymantria monacha, and Pieris brassicae;*

Examples from the Coleoptera order are *Blitophaga undata, Melanotus communis, Limonius californicus, Agriotes lineatus, Agriotes obscurus, Agrilus sinuatus, Meligethes aeneus, Atomaria linearis, Epilachna varicestris, Phyllopertha horticola, Popillia japonica, Melolontha melolontha, Melolontha hippocastani, Amphimallus solstitialis, Crioceris asparagi, Lema melanopus, Leptinotarsa decemlineata, Phaedon cochleariae, Phyllotreta nemorum, Chaetocnema tibialis, Phylloides chrysocephala, Diabrotica 12-punctata, Cassida nebulosa, Bruchus lentis, Bruchus rufimanus, Bruchus pisorum, Sitona lineatus, Otiorrhynchus sulcatus, Otiorrhynchus ovatus, Hylobies abietis, Byctiscus betulae, Anthonomus pomorum, Anthonomus grandis, Ceuthorrhynchus assimilis, Ceuthorrhynchus napi, Sitophilus granaria, Anisandrus dispar, Ips typographus,* and *Blastophagus piniperda;*

Examples from the Diptera order are *Lycoria pectoralis, Mayetiola destructor, Dasyneura brassicae, Contarinia tritici, Haplodiplosis equestris, Tipula paludosa, Tipula oleracea, Dacus cucurbitae, Dacus oleae, Ceratitis capitata, Rhagoletis cerasi, Rhagoletis pomonella, Anastrepha ludens, Oscinella frit, Phorbia coarctata, Phorbia antiqua, Phorbia brassicae, Pegomya hyoscyami, Anopheles maculipennis, Culex pipiens, Aedes aegypti, Aedes vexans, Tabanus bovinus, Tipula paludosa, Musca domestica, Fannia canicularis, Muscina stabulans, Glossina morsitans, Oestrus ovis, Chrysomya macellaria, Chrysomya hominivorax, Lucilia cuprina, Lucilia sericata,* and *Hypoderma lineata;*

Examples from the Hymenoptera order are *Athalia rosae, Hoplocampa minuta, Monomorium pharaonis, Solenopsis geminata,* and *Atta sexdens;*

Examples from the Heteroptera order are *Nezara viridula, Eurygaster integriceps, Blissus leucopterus, Dysdercus cingulatus, Dysdercus intermedius, Piesma quadrata,* and *Lygus pratensis;*

Examples from the Homoptera order are *Perkinsiella saccharicida, Nilaparvata lugens, Empoasca fabae, Psylla mali, Psylla piri, Trialeurodes vaporariorum, Aphis fabae, Aphis pomi, Aphis sambuci, Aphidula nasturtii, Cerosipha gossypii, Sappaphis mali, Sappaphis mala, Dysaphis radicola, Brachycaudus cardui, Brevicoryne brassicae, Phorodon humuli, Rhopalomyzus ascalonicus, Myzodes persicae, Myzus cerasi, Dysaulacorthum pseudosolani, Acyrthosiphon onobrychis, Macrosiphon rosae, Megoura viciae, Schizoneura lanuginosa, Pemphigus bursarius, Dreyfusia nordmannianae, Dreyfusia piceae, Adelges laricis,* and *Viteus vitifolii;*

Examples from the Isoptera order are *Reticulitermes lucifugus, Calotermes flavicollis, Leucotermes flavipes,* and *Termes natalensis;*

Examples from the Orthoptera order are *Forficula auricularia, Acheta domestica, Gryllotalpa gryllotalpa, Tachycines asynamorus, Locusta migratoria, Stauronotus maroccanus, Schistocerca peregrina, Nomadacris septemfasciata, Melanoplus spretus, Melanoplus femur-rubrum, Blatta orientalis, Blattella germanica, Periplaneta americana,* and *Blabera gigantea.*

Examples of mites and ticks (Acarina) belonging to the Arachnida class are *Tetranychus telarius, Tetranychus pacificus, Paratetranychus pilosus, Bryobia praetiosa, Ixodes ricinus, Ornithodorus moubata, Amblyomma americanum, Dermacentor silvarum,* and *Boophilus microplus.*

Examples from the Nemathelminthes class are root-knot nematodes, e.g., *Meloidogyne incognita, Meloidogyne hapla,* and *Meloidogyne javanica,* cyst-forming nematodes, e.g., *Heterodera rostochiensis, Heterodera schachtii, Heterodera avenae, Heterodera glycines,* and *Heterodera trifolii,* and stem and leaf eelworms, e.g., *Ditylenchus dipsaci, Ditylenchus destructor, Pratylenchus neglectus, Pratylenchus penetrans, Pratylenchus goodeyi, Pratylenchus curvitatus* and *Tylenchorhynchus dubius, Tylenchorhynchus claytoni, Rotylenchus robustus, Heliocotylenchus multicinctus, Radopholus similis, Belonolaimus longicaudatus, Longidorus elongatus,* and *Trichodorus primitivus.*

The active ingredients may be applied for instance as such, or in the form of formulations or application forms prepared therefrom, e.g., directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Examples of formulations are given below.

I. 5 parts by weight of compound no. 4 is intimately mixed with 95 parts by weight of particulate kaolin. A dust is obtained containing 5% by weight of the active ingredient.

II. 30 parts by weight of compound no. 3 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

III. 10 parts by weight of compound no. 10 is dissolved in a mixture consisting of 90 parts by weight of xylene, 6 parts by weight of the adduct of 8 to 10 moles of ethylene oxide and 1 mole of oleic acid-N-monoethanolamide, 2 parts by weight of the calcium salt of dodecylbenzenesulfonic acid, and 2 parts by weight of the adduct of 40 moles of ethylene oxide and 1 mole of castor oil.

IV. 20 parts by weight of compound no. 7 is dissolved in a mixture consisting of 60 parts by weight of cyclohexanone, 30 parts by weight of isobutanol, 5 parts by weight of the adduct of 7 moles of ethylene oxide and 1 mole of isooctylphenol, and 5 parts by weight of the adduct of 40 moles of ethylene oxide and 1 mole of castor oil.

V. 80 parts by weight of compound no. 8 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

The active ingredient concentrations in the finished formulations may vary over a wide range. Generally, they are from 0.0001 to 10, and preferably from 0.01 to 1, %. The active ingredients may also successfully be used in the ultra-low-volume (ULV) method, where it is possible to apply formulations containing more than 95 wt% of active ingredient, or even the active ingredient without additives.

In the open, the amount of active ingredient applied is for example from 0.001 to 10, and preferably from 0.01 to 1, kg/ha.

There may be added to the active ingredients (if desired, immediately before use (tankmix)) oils of various types, herbicides, fungicides, other insecticides and bactericides. These agents may be added to the active ingredients according to the invention in a weight ratio of from 1:10 to 10:1.

Examples of active ingredients which may be admixed are as follows: 1,2-dibromo-3-chloropropane, 1,3-dichloropropene, 1,3-dichloropropene+1,2-dichloropropane, 1,2-dibromoethane, 2-sec-butylphenyl-N-methylcarbamate, o-chlorophenyl-N-methylcarbamate, 3-isopropyl-5-methylphenyl-N-methylcarbamate, o-isopropoxyphenyl-N-methylcarbamate, 3,5-dimethyl-4-methylmercaptophenyl-N-methylcarbamate, 4-dimethylamino-3,5-xylyl-N-methylcarbamate, 2-(1,3-dioxolan-2-yl)-phenyl-N-methylcarbamate, 1-naphthyl-N-methylcarbamate, 2,3-dihydro-2,2-dimethylbenzofuran-7-yl-N-methylcarbamate, 2,2-dimethyl-1,3-benzodioxol-4-yl-N-methylcarbamate, 2-dimethylamino-5,6-dimethyl-4-pyrimidinyldimethylcarbamate, 2-methyl-2-(methylthio)-propion aldehyde-O-(methylcarbamoyl)-oxime, S-methyl-N-[(methylcarbamoyl)-oxy]-thioacetimidate, methyl-N',N'-dimethyl-N-[(methyl-carbamoyl)-oxy]-1-thiooxamidate, N-(2-methyl-4-chlorophenyl)-N'N'-dimethylformamidine, tetrachlorothiophene, 1-(2,6-difluorobenzyl)-3-(4-chlorophenyl)-urea, O,O-dimethyl-O-(p-nitrophenyl)-phosphorothioate, O,O-diethyl-O-(p-nitrophenyl)-phosphorothioate, O-ethyl-O-(p-nitrophenyl)-phenyl-phosphonothioate, O,O-dimethyl-O-(3-methyl-4-nitrophenyl)-phosphorothioate, O,O-diethyl-O-(2,4-dichlorophenyl)-phosphorothioate, O-ethyl-O-(2,4-dichlorophenyl)-phenylphosphonothioate, O,O-dimethyl-O-(2,4,5-trichlorophenyl)-phosphorothioate, O-ethyl-O-(2,4,5-trichlorophenyl)-ethyl-phosphonothioate, O,O-dimethyl-O-(4-bromo-2,5-dichlorophenyl)-phosphorothioate, O,O-dimethyl-O-(2,5-dichloro-4-iodophenyl)-phosphorothioate, O,O-dimethyl-O-(3-methyl-4-methylthiophenyl)-phosphorothioate, O-ethyl-O-(3-methyl-4-methylthiophenyl)-isopropylphosphoramidate, O,O-diethyl-O-[p-(methylsulfynyl)-phenyl]-phosphorothioate, O-ethyl-S-phenylethyl-phosphonodithioate, O,O-diethyl-[2-chloro-1-(2,4-dichlorophenyl)-vinyl]-phosphate, O,O-dimethyl-[-2-chloro-1-(2,4,5-trichlorophenyl)]-vinylphosphate, O,O-dimethyl-S-(1-phenyl)-ethylacetate phosphorodithioate, bis-(dimethylamino)-fluorophosphine oxide, octamethyl-pyrophosphoramide, O,O,O,O-tetraethyldithiopyrophosphate, S-chloromethyl-O,O-diethyl-phosphorodithioate, O-ethyl-S,S-dipropyl-phosphorodithioate, O,O-dimethyl-O-2,2-dichlorovinylphosphate, O,O-dimethyl-1,2-dibromo-2,2-dichloroethylphosphate, O,O-dimethyl-2,2,2-trichloro-1-hydroxyethylphosphonate, O,O-dimethyl-S-[1,2-biscarbethoxyethyl-(1)]-phosphorodithioate, O,O-dimethyl-O-(1-methyl-2-carbomethoxyvinyl)-phosphate, O,O-dimethyl-S-(N-methylcarbamoylmethyl)-phosphorodithioate, O,O-dimethyl-S-(N-methylcarbamoylmethyl)-phosphorothioate, O,O-dimethyl-S-(N-methoxyethylcarbamoylmethyl)-phosphorodithioate, O,O-dimethyl-S-(N-formyl-N-methylcarbamoylmethyl)-phosphorodithioate, O,O-dimethyl-O-[1-methyl-2-(methylcarbamoyl)-vinyl]-phosphate, O,O-dimethyl-O-[(1-methyl-2-dimethylcarbamoyl)-vinyl]-phosphate, O,O-dimethyl-O-[(1-methyl-2-chloro-2-diethylcarbamoyl)-vinyl]-phosphate, O,O-diethyl-S-(ethylthiomethyl)-phosphorodithioate, O,O-diethyl-S-[(p-chlorophenylthio)-methyl]-phosphorodithioate, O,O-dimethyl-S-(2-ethylthioethyl)-phosphorothioate, O,O-dimethyl-S-(2-ethylthioethyl)-phosphorodithioate, O,O-dimethyl-S-(2-ethylsulfynylethyl)-phosphorothioate, O,O-diethyl-S-(2-ethylthioethyl)-phosphorodithioate, O,O-diethyl-S-(2-ethylsulfynylethyl)-phosphorothioate, O,O-diethylthiophosphoryliminophenyl-acetonitrile, O,O-diethyl-S-(2-chloro-1-phthalimidoethyl)-phosphorodithioate, O,O-diethyl-S-[6-chlorobenzoxazolon-(2)-yl-(3)]-methyldithiophosphate, O,O-dimethyl-S-[2-methoxy-1,3,4-thiadiazol-5[4H]-onyl-(4)-methyl]-phosphorodithioate, O,O-diethyl-O-[3,5,6-trichloropyridyl-(2)]-phosphorothioate, O,O-diethyl-O-(2-pyrazinyl)-phosphorothioate, O,O-diethyl-O-[2-isopropyl-4-methylpyrimidinyl-(6)]-phosphorothioate, O,O-diethyl-O-[2-(diethylamino)-6-methyl-4-pyrimidinyl]-thionophosphate, O,O-dimethyl-S-(4-oxo-1,2,3-benzotriazin-3-[4H]-yl-methyl)-phosphorodithioate, O,O-dimethyl-S-[(4,6-diamino-1,3,5-triazin-2-yl)-methyl]-phosphorodithioate, O,O-diethyl-(1-phenyl-1,2,4-triazol-3-yl)-thionophosphate, O,S-dimethylphosphoroamidothioate, O,S-dimethyl-N-acetylphosphoramidothioate, alpha-hexachlorocyclohexane, 1,1-di-(p-methoxyphenyl)-2,2,2-trichloroethane, 6,7,8,9,10,10-hexachloro-1,5,5a,6,9,9a-hexahydro-6,9-methano-2,4,3-benzodioxathiepine-3-oxide, pyrethrins, DL-2-a llyl-3-methyl-cyclopenten-(2)-on-(1)-yl-(4)-DL-cis,trans-chrysanthemate, 5-benzylfuryl-(3)-methyl-DL-cis,trans-chrysanthemate, 3-phenoxybenzyl($\pm$)-cis,trans-2,2-dimethyl-3-(2,2-dichlorovinyl)-cyclopropanecarboxylate, alpha-cyano-3-phenoxybenzyl($\pm$)-cis,trans-2,2-dimethyl-3-(2,2-dichlorovinyl)-cyclopropanecarboxylate, (s)-alpha-cyano-3-phenoxybenzyl-cis(1R,3R)-2,2-dimethyl-3-(2,2-dibromovinyl)-cyclopropanecarboxylate, 3,4,5,6-tetrahydrophthalimidoethyl-DL-cis,trans-chrysanthemate, 2-methyl-5-(2-propynyl)-3-furylmethylchrysanthemate, and alpha-cyano-3-phenoxybenzyl-alpha-isopropyl-4-chlorophenylacetate.

Manufacturing example

O-(O-ethyl-S-n-propylphosphoryl)-O-(N-methylcarbamoyl)-pyrocatechol (compound no. 4)

While stirring, 203 g (1 mol) of O-ethyl-S-n-propyl-phosphoryl chloride is added to 167 g (1 mol) of N-methylcarbamoylpyrocatechol in 1000 ml of acetonitrile; 101 g (1 mol) of triethylamine is dripped in at room temperature and the mixture is heated at 50° C. for 2 hours. After the mixture has cooled it is suction filtered, the filtrate is concentrated under reduced pressure, the residue is taken up in 600 ml of methylene chloride, and the solution is washed three times with a 10% strength $Na_2CO_3$ solution and again three times with water. After drying over sodium sulfate the solvent is removed under reduced pressure. There is obtained 163 g (49%) of O-(O-ethyl-S-n-propylphosphoryl)-O-(N-methylcarbamoyl)-pyrocatechol (compound no. 4) as an oil.

The compounds I in the table below for which NMR spectra are given were obtained in accordance with the above example; the other compounds of the formula I may be obtained in the same way.

To characterize the compounds I according to the invention, $^1$H-NMR spectra were taken in $CDCl_3$.

TABLE

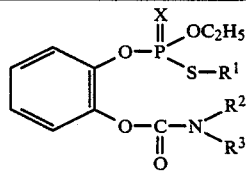
(I)

| Compound No. | $R^1$ | $R^2$ | $R^3$ | X | Field strength [MHz] | Signals δ [ppm] | Refractive Index |
|---|---|---|---|---|---|---|---|
| 1 | sec.-$C_4H_9$ | $CH_3$ | H | S | | 0.98 (m, 3H); 1.38 (m, 6H); 1.68 (m, 2H); 2.82 (d, 3H); 3.40 (m, 1H); 4.24 (m, 2H); 5.37 (bd, 1H); 7.13–7.55 (m, 4H); | |
| 2 | iso-$C_4H_9$ | $CH_3$ | H | S | | 1.0 (d, 6H); 1.36 (t, 3H); 1.90 (m, 1H); 2.82 (d, 3H); 2.90 (m, 2H); 4.25 (m, 2H); 5.44 (bd, 1H) 7.13–7.55 (m, 4H); | |
| 3 | n-$C_3H_7$ | $CH_3$ | H | S | | 1.0 (t, 3H); 1.40 (t, 3H); 1.70 (m, 2H); 2.90 (d, 3H); 2.96 (m, 2H); 4.27 (m, 2H); 5.20 (bd, 1H); 7.15–7.50 (m, 4H); | |
| 4 | n-$C_3H_7$ | $CH_3$ | H | O | | 0.95 (t, 3H); 1.37 (t, 3H); 1.70 (m, 2H); 2.75 (m, 5H); 4.25 (m, 2H); 5.55 (bs, 1H); 7.10–7.50 (m, 4H); | |
| 5 | sec.-$C_4H_9$ | $CH_3$ | H | O | | | |
| 6 | iso-$C_4H_9$ | $CH_3$ | H | O | | | |
| 7 | iso-$C_4H_9$ | $CH_3$ | $CH_3$ | S | | 1.0 (m, 6H); 1.38 (t, 3H); 1.92 (m, 1H); 2.87 (m, 2H); 3.0 (s, 3H); | |

TABLE-continued

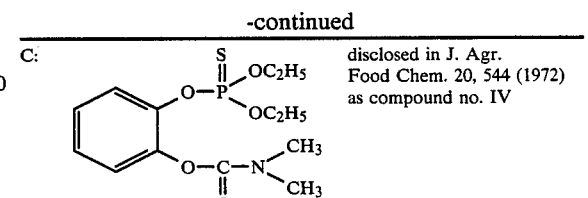

(I)

| Compound No. | R¹ | R² | R³ | X | Field strength [MHz] | Signals δ [ppm] | Refractive Index |
|---|---|---|---|---|---|---|---|
| | | | | | | 3.16 (s, 3H); 4.25 (m, 2H); 7.15–7.50 (m, 4H); | |
| 8 | sec.-$C_4H_9$ | $CH_3$ | $CH_3$ | S | | 1.0 (m, 3H); 1.38 (m, 6H); 1.72 (m, 2H); 3.02 (s, 3H); 3.17 (s, 3H); 3.44 (m, 1H); 4.26 (m, 2H); 7.15–7.50 (m, 4H); | |
| 9 | n-$C_3H_7$ | $CH_3$ | $CH_3$ | S | | 1.0 (t, 3H); 1.38 (t, 3H); 1.72 (m, 2H); 2.90 (m, 2H); 3.00 (s, 3H); 3.15 (s, 3H); 4.23 (m, 2H); 7.15–7.50 (m, 4H); | |
| 10 | n-$C_3H_7$ | $CH_3$ | $CH_3$ | O | | 0.96 (t, 3H); 1.40 (t, 3H); 1.68 (m, 2H); 2.88 (m, 2H); 3.00 (s, 3H); 3.16 (s, 3H); 4.25 (m, 2H); 7.15–7.50 (m, 4H); | |
| 11 | sec.-$C_4H_9$ | $CH_3$ | $CH_3$ | O | | | |
| 12 | iso-$C_4H_9$ | $CH_3$ | $CH_3$ | O | | 0.96 (d, 6H); 1.38 (t, 3H); 1.85 (m, 1H); 2.78 (m, 2H); 3.00 (s, 3H); 3.14 (s, 3H); 4.25 (m, 2H); 7.10–7.50 (m, 4H); | |
| 13 | iso-$C_4H_9$ | $OC_2H_5$ | H | O | | 0.95 (d, 6H); 1.30 (t, 3H); 1.37 (t, 3H); 1.85 (m, 1H); 2.80 (m, 2H); 4.03 (q, 2H); 4.27 (m, 2H); 7.20–7.50 (m, 4H); 8.35 (bs, 1H); | |
| 14 | n-$C_3H_7$ | $OC_2H_5$ | H | O | | 0.97 (m, 3H); 1.27 (t, 3H); 1.37 (t, 3H); 1.68 (m, 2H); 2.90 (m, 2H); 4.00 (q, 2H); 4.27 (m, 2H); 7.15–7.50 (m, 4H); 8.87 (bs, 1H); | |
| 15 | sec.-$C_4H_9$ | $OC_2H_5$ | H | O | | | |
| 16 | iso-$C_4H_9$ | $OC_2H_5$ | H | S | | | |
| 17 | n-$C_3H_7$ | $OC_2H_5$ | H | S | | 0.98 (t, 3H); 1.30 (t, 3H); 1.40 (t, 3H); 1.88 (m, 2H); 2.96 (m, 2H); 4.07 (q, 2H); 4.25 (m, 2H); 7.15–7.50 (m, 4H); 8.04 (bs, 1H); | |
| 18 | n-$C_3H_7$ | H | H | O | | 0.95 (m, 3H); 1.25 (m, 3H); 1.63 (m, 2H); 2.75 (m, 2H); 4.10 (m, 2H); 6.65–6.90 (m, 4H); 7.50 (b, 2H) | $n_D^{21} = 1.5255$ |
| 19 | sec.-$C_4H_7$ | H | H | O | | | |
| 20 | iso-$C_4H_9$ | H | H | O | | | |

Use examples

In the following examples, the action of compounds according to the invention, or agents containing them, on pests was compared with that of the following art compounds:

A: 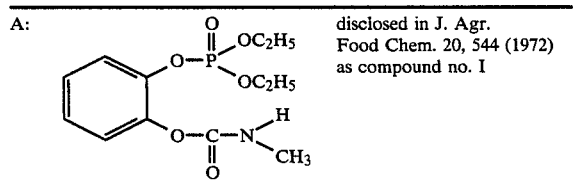  disclosed in J. Agr. Food Chem. 20, 544 (1972) as compound no. I

B: 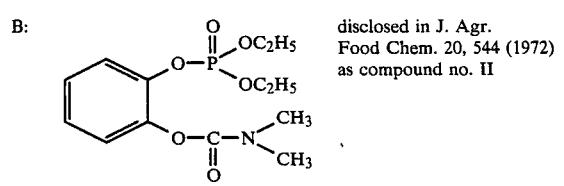  disclosed in J. Agr. Food Chem. 20, 544 (1972) as compound no. II

C: disclosed in J. Agr. Food Chem. 20, 544 (1972) as compound no. IV

The concentrations at which the candidate compounds exhibit 100% kill or inhibition are the minimum concentrations. At least one replicate was used for each concentration.

Example A

Tetranychus telarius (spider mite); contact action-spray test

Potted bush beans which had developed the first pair of true leaves and were heavily infested with all stages of the spider mite Tetranychus telarius were sprayed to runoff in a spray cabinet with aqueous formulations of the active ingredients. The plants were placed on a rotating disc and sprayed from all sides with 50 ml of spray liquor. Spraying lasted for about 22 seconds. After 8 days, the plants were inspected for living spider mites.

In this experiment, the lethal dose of compounds nos. 1, 2, 3, 4, 9, 10, 12 and 14 was not more than 0.04 wt%. A dose of 0.1 wt% of the comparative agents A, B and C had no effect.

Example B

Tetranychus telarius (spider mite); contact and residual action

Potted bush beans which had developed the second pair of true leaves were sprayed to runoff in a spray cabinet with aqueous formulations of the active ingredients. The plants were placed on a rotating disc and sprayed from all sides with 50 ml of spray liquor. Spraying lasted for about 22 seconds. After 24 hours, the plants were infected with leaf pieces heavily infested with spider mites. Plant attack was assessed after 12 days.

In this experiment, the lethal dose of compounds nos. 2, 3, 4, 7, 10 and 12 was 0.1 wt% at most; comparative compounds A, B and C had no effect at this application rate.

Example C

Plutella maculipennis (diamondback moth); effect of ingested food

Leaves of young cabbage plants were dipped for 3 seconds in aqueous emulsions of the active ingredients, and placed, after excess liquor had been briefly allowed to drip off, on moist filter papers in Petri dishes. 10 caterpillars of the fourth stage were then placed on each leaf. The kill rate was assessed after 48 hours.

In this experiment, the lethal dose of compound no. 9 was 0.004 wt%. Compounds nos. 1, 3, 4 and 10 achieved 80% kill at a rate of not more than 0.002 wt%. Comparative compounds A, B and C had no effect at a rate of 0.1 wt%.

Example D

Aphis fabae; contact action-spray test

Potted bush beans (Vicia faba) heavily infested with colonies of bean aphids were sprayed to runoff in a spray cabinet with aqueous formulations of the active ingredients. Assessment took place after 24 hours.

In this experiment, the lethal dose of compounds nos. 1, 3, 7 and 8 was not more than 0.01 wt%. The lethal dose of comparative compound A was 0.1 wt%, and comparative compounds B and C had no effect at 0.1 wt%.

We claim:

1. O-(O-ethyl-S-alkylphosphoryl)-O-(carbamoyl)-pyrocatechol derivatives of the general formula I

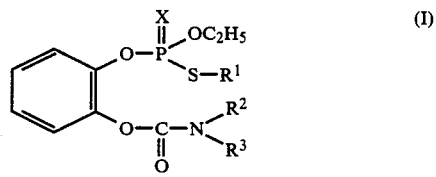

where $R^1$ is $C_1$–$C_4$-alkyl, $R^2$ is hydrogen, $C_1$–$C_4$-alkyl or $C_1$–$C_4$-alkoxy, $R^3$ is hydrogen or $C_1$–$C_4$-alkyl, and X is oxygen or sulfur.

2. O-(O-ethyl)-S-n-propylphosphoryl-O-N-methylcarbamoyl)-pyrocatechol.

3. A pesticide containing a pesticidally effective amount of an O-(O-ethyl-S-alkylphosphoryl)-O-(carbamoyl)-pyrocatechol derivative of the formula I as set forth in claim 1 and solid carriers.

4. A pesticide as set forth in claim 3, containing from 0.1 to 95 wt% of an O-(O-ethyl-S-alkylphosphoryl)-O-(carbamoyl)-pyrocatechol derivative I.

5. A process for combating pests, wherein the pests, or the areas or spaces to be kept free from pests are treated with a pesticidally effective amount of an O-(O-ethyl-S-alkylphosphoryl)-O-(carbamoyl)pyrocatechol derivative of the formula I as set forth in claim 1.

* * * * *